United States Patent [19]

Jelly

[11] Plant 4,412

[45] May 15, 1979

[54] YELLOW ROSE PLANT 66-73-YG

[75] Inventor: Robert G. Jelly, Richmond, Ind.

[73] Assignee: E. G. Hill Co., Inc., Richmond, Ind.

[21] Appl. No.: 911,348

[22] Filed: Jun. 1, 1978

[51] Int. Cl.[2] ..... A01H 5/00

[52] U.S. Cl. ..... Plt./15

[58] Field of Search ..... Plt./15

*Primary Examiner*—Robert E. Bagwill

*Attorney, Agent, or Firm*—Chas. W. Rummler

[57] ABSTRACT

A yellow rose seedling intended for greenhouse culture and the production of cut flowers, the new plant being of the grandiflora class and particularly distinguished by its continuous and abundant production of large high centered blossoms, its vigorous upright growth habit with many multiple breaking canes topped by a long tapered bud of excellent yellow flower color, and its low incidence of winter blind.

1 Drawing Figure

BACKGROUND OF THE NEW PLANT

This new variety of yellow rose is a result of my crossing "Golden Fantasie" (P.P. 3272) with "Coed" (P.P. 3166) in September of 1971 at Richmond, Ind., with the object of eliminating the winter blind produced by "Golden Fantasie" and to increase the stem length of "Coed". This seedling first flowered in the Spring of 1972 and its improved growth habit together with the very excellent appearance of its buds and flowers led to my reproducing the plant by grafting for test purposes at Richmond, Ind., with favorable results. Further propagation of this new plant, through successive generations, by grafting at Richmond, Ind., and at Livermore, Calif., has demonstrated that its distinctive characteristics hold true and appear to be firmly fixed.

DESCRIPTION OF THE DRAWING

This new yellow rose cultivar is illustrated by the accompanying full color photographic drawing which shows buds in several stages of opening, a face view of a fully opened blossom, specimens of typical leaves, a specimen of young wood with new leaves, a specimen of wood and leaves with a newly formed bud, and typical specimens of mature wood.

DESCRIPTION OF THE NEW PLANT

The following is a detailed description of my new yellow rose variety based upon observations of plants and cut flowers grown and flowered in greenhouse at Richmond, Ind., in 1976, the color descriptions being according to the R.H.S. Colour Chart (RHS) and the Robert S. Wilson Horticultural Colour Chart, both charts being as published by The Royal Horticultural Society of London, England.

THE PLANT

Origin: Seedling, identified as #66-73-YG.

Parentage:

*Seed parent.*—Golden Fantasie (P.P. 3272).

*Pollen parent.*—Coed (P.P. 3166).

Classification: Grandiflora.

Type: Seedling for greenhouse culture and for cut flowers.

Form: Bush.

Growth (in greenhouse): Vigorous, with upright and much branched habit.

Canes: Multiple breaking and medium large in diameter.

Main Stems:

*Color.*—Spinach Green 0960/1 (W), pencilled with Green 136B (RHS).

*Thorns.*—Several to many, of long length, straight and angled downward from a long and broad base. Color: Greyed Orange 165B (RHS), shaded with 165A (RHS).

Prickles and hairs: None.

Foliage: Quantity — Abundant.

*Leaves.*—Compound and odd pinnate. Size: Medium to large.

*Leaflets.*—3, 5 or 7 in number. Shape: Oval with obtuse base, cuspidate apex and irregularly serrate margin. Aspect: Moderately thick and leathery. Appearance: Glossy. Color: Mature upper surface — Shades of Greyed Purple 185A and 185B (RHS) along the mid-vein blending to a shade between Ivy Green 0001060/3 (W) and Parsley Green 00962 (W), bordered with Dahlia Purple 931 (W), the whole leaf being mottled with these colors. Mature under surface — Leek Green 000858/1 (W) in general, mottled with Greyed Purple 184C (RHS) and bordered with Greyed Purple 187A (RHS), the mid-vein being Greyed Red 182C (RHS). Young upper surface — Mainly Maroon 1030 (W), becoming mottled with Green 143C and 143B (RHS) as the leaf matures. Young under surface: Maroon 1030/3 (W), with highlights of Garnet Lake 828 (W), and Maroon 1030 (W) on the margins. Rachis: Heavy, with the upper side grooved and prickly and the under side thorny. Stipules: Long and narrow, with short points which turn out at an angle less than 45° and are not recurved toward the stem.

THE BUD

Before calyx breaks:

*Size.*—Medium large.

*Form.*—Long pointed, with conspicuous neck and with foliaceous appendages on the surface of the bud which have slender bristle-like parts extending beyond the tip of the bud for a distance equal to $\frac{3}{4}$ or more of the bud length.

*Color of calyx.*—Yellow Green 144B (RHS) at the center of the sepals blending to Spinach Green 0960/1 (W) and with the foliaceous parts being Green 141B (RHS), some washed or bordered with Greyed Purple 183B (RHS).

As calyx breaks:

*Outside petal color.*—Primrose Yellow 601 (W).

As first petals open:

*Size.*—Medium small.

*Form.*—Long pointed.

*Color of petal.*—Outside surface — Lemon Yellow 4/1 (W). Inside surface — Aureolin 3 (W).

Opening: The bud opens well in greenhouse.

Sepals: Permanent and of medium length.

*Color.*—Inside of sepals — Pod Green 061/1 (W) at the point of attachment, blending to Green 138B and 138A (RHS). Outside of sepals — Green 144C (RHS) at the point of attachment, blending to Spinach Green 0960 (W) with tips of Greyed Purple 183C (RHS). Inside of foliaceous parts — Green 139B (RHS) with tips of Greyed Purple 183C (RHS).

Peduncle: Short, strong and erect, and of medium diameter.

*Bark.*—Entirely smooth. Color: Yellow Green 144C shaded with 144B (RHS) and Oxblood Red 00823/3 (W).

*Thorns, prickles and hairs.*—None.

THE FLOWER

Blooming habit: Continuous in greenhouse with an abundant production of long tapered buds.

Borne: One to several on a single stem, disbudded for commercial production to provide single flowers on strong, medium long stems.

Size: 3½ to 4 inches in diameter when fully opened.

Form: High centered at first, then becoming open with the petals remaining rolled outward. At maturity, the petals become tightly rolled outward.

Petalage: Double, with 18 to 22 petals regularly arranged.

*Shape.*—All petals — Ovate, with a flat apex.

*Aspect.*—Moderately thick and leathery.

*Appearance.*—Satiny, both inside and outside.

Color:

A. The following is a color description of a newly opened greenhouse flower grown in the month of December:

*Outside petals.*—Outer surface — Yellow 12B (RHS) with highlights of Yellow 13B (RHS). Inner surface — Yellow 12A (RHS) at point of attachment, shaded to Yellow 7C (RHS) which is the main color.

*Intermediate petals.*—Outside surface — Yellow 12B (RHS). Inside surface — Yellow 9A (RHS).

*Inner petals.*—Outside surface — Aureolin 3/1 (W). Inside surface — Aureolin 3 (W).

B. The following is a description of a rose opened for 3 days in greenhouse in the month of December:

*Outside petals.*—Outer surface — Yellow 8A (RHS). Inside surface — Yellow 9A (RHS) at point of attachment, shaded to the main color Yellow 7B (RHS).

*Intermediate petals.*—Outside surface — Canary Yellow 2/2 (W). Inside surface — Yellow 7A (RHS) at point of attachment, shaded to Yellow 6B (RHS), the main color.

*Inner petals.*—Outer surface — Aureolin 3/1 (W). Inner surface — Aureolin 3 (W).

General Color Effect of Open Blooms:

*Newly opened flower.*—Yellow 9B (RHS).

*Three days opened flower.*—Canary Yellow 2/2 (W).

Note: These colors may be modified by being bordered, margined, pencilled, striped, dotted, blotched, shaded, washed, or tinted with other colors.

Fragrance: Strong sweetbriar.

Persistence: The petals hang on and dry.

Effect of weather: Under hot dry conditions, both the bud and flower are slightly smaller and the flower color tends to fade to Yellow 4C (RHS).

Flower longevity: Greenhouse grown cut flowers — About 8 days at living room temperatures in December.

REPRODUCTIVE ORGANS

Stamens: Many in number, arranged regularly about the pistils and mixed with petaloids.

*Filaments.*—Of varied length, most with anthers. Color: Short filaments — Red 53B (RHS) at the base, fading to Red 53C (RHS) and Red 53D (RHS) just under the pollen cup. Longer filaments — Greyed Red 179B (RHS) at the base, shaded to Yellow 11A (RHS), which is the main color.

*Anthers.*—Large, all open at once. Color: Pollen cup — Greyed Yellow 162B (RHS), with Greyed Orange 175B (RHS) on the margin.

*Pollen.*—Abundant. Color: Greyed Orange 163A (RHS).

Pistils: Number — Medium.

*Styles.*—Uneven, of medium length, very thin and bunched. Color: Yellow Green 149D (RHS), almost transparent, at the base, shaded to Red 50C (RHS), some having blotches of Red 47A (RHS).

*Stigmas.*—Color — Greyed Orange 163C (RHS).

Ovaries: All encased in calyx.

Hips: Medium flat, slightly pear-shaped with a conspicuous neck, very smooth and with thick fleshy walls.

*Color.*—Persimmon Orange 710 (W), blending through 710/1 and 710/2 (W), with streaks and spots of Green 144C (RHS).

Seeds: Many, of medium size.

This new rose plant cultivar is a superior plant when it is judged on a vigorous upright habit of growth and its many multiple breaking canes each topped by a long tapered bud of excellent yellow flower color. It is an improvement over its seed parent "Golden Fantasie" (U.S. Plant Pat. No. 3,272) because of its low incidence of winter blind and because of its large increase in productivity picked up from its pollen parent "Coed" (U.S. Plant Pat. No. 3,166).

Also this cultivar is much superior to its pollen parent because of its longer stem, its long tapered bud, and its very free, upright growth habit.

I claim:

1. A new and distinct yellow rose cultivar, substantially as herein shown and described, characterized by its vigorous and upright habit of growth and its many multiple breaking canes which become topped by long tappered buds, and by its free and continuous flower production under greenhouse culture.

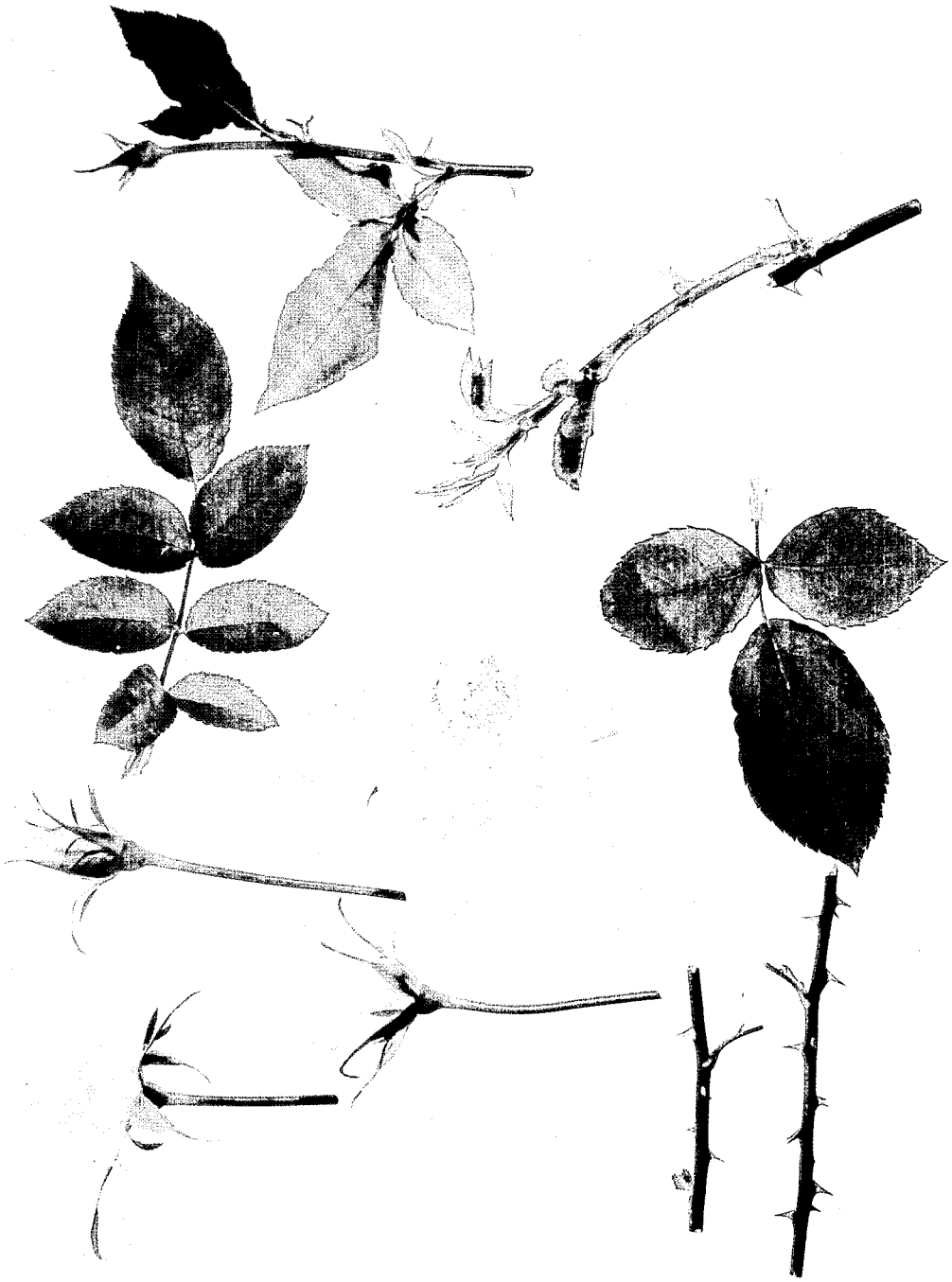

* * * * *